US006187778B1

(12) United States Patent
Dow et al.

(10) Patent No.: US 6,187,778 B1

(45) Date of Patent: Feb. 13, 2001

(54) 4-AMINOPYRROLE (3, 2-D) PYRIMIDINES AS NEUROPEPTIDE Y RECEPTOR ANTAGONISTS

(75) Inventors: Robert Lee Dow, Waterford; Marlys Hammond, Salem, both of CT (US)

(73) Assignee: Pfizer Inc., New York, NY (US)

(*) Notice: Under 35 U.S.C. 154(b), the term of this patent shall be extended for 0 days.

(21) Appl. No.: 09/380,901

(22) PCT Filed: Jul. 10, 1998

(86) PCT No.: PCT/IB98/01053

§ 371 Date: Sep. 7, 1999

§ 102(e) Date: Sep. 7, 1999

(87) PCT Pub. No.: WO99/07703

PCT Pub. Date: Feb. 18, 1999

Related U.S. Application Data

(60) Provisional application No. 60/054,734, filed on Aug. 5, 1997, now abandoned.

(51) Int. Cl.$^7$ .......................... A61K 31/519; C07D 487/04

(52) U.S. Cl. .......................... 514/258; 514/258; 544/280

(58) Field of Search .......................... 514/258; 544/280

(56) References Cited

U.S. PATENT DOCUMENTS

| | | | | |
|---|---|---|---|---|
| 3,274,213 | | 9/1966 | Lednicer et al. | 260/326.5 |
| 4,229,453 | * | 10/1980 | Roth et al. | 424/251 |
| 5,235,053 | * | 8/1993 | Barnett et al. | 544/280 |
| 5,284,971 | | 2/1994 | Walker et al. | 562/429 |
| 5,328,910 | * | 7/1994 | Hrgreaves | 514/258 |
| 5,569,674 | | 10/1996 | Yokoyama et al. | 514/539 |
| 5,576,337 | | 11/1996 | Bruns et al. | 514/324 |
| 5,644,057 | * | 7/1997 | Yuan et al. | 544/280 |
| 5,686,457 | * | 11/1997 | Traxler et al. | 514/258 |
| 5,869,485 | * | 2/1999 | Missbach | 514/234.2 |
| 5,877,178 | * | 3/1999 | Gangjee | 514/258 |

FOREIGN PATENT DOCUMENTS

| | | | | |
|---|---|---|---|---|
| 0759441 | | 2/1997 | (EP) | C07K/14/47 |
| 0438261 | * | 1/1990 | (JP) . | |
| WO 9614307 | | 5/1996 | (WO) | C07D/295/02 |
| WO 9725041 | | 7/1997 | (WO) | A61K/31/415 |

OTHER PUBLICATIONS

Wahlestedt, C., et al, *Regulatory Peptides*, 13 (1986) pp. 307–318, "Evidence for different pre–and post–junctional receptors for neuropeptide Y and related peptides".

Grundemar, L., et al, *Br. J. Pharmacol. Exp. Ther.*, 105:45–50 (1992), "Characterization of vascular neuropeptide Y receptors".

McAuley, M.A., et al, The Journal of Pharmcology and Experimental Therapeutics, vol. 261, No. 3, pp. 863–868, Possible Location and Function of Neuropeptide Y Receptor Subtypes in the Rat Mesenteric Arterial Bed.

Flood, J.F., et al, *Peptides*, vol. 10, pp. 963–966, "Dissociation of the Effects of Neuropeptide Y on Feeding and Memory: Evidence for Pre–and Postsynaptic Mediation".

Leibowitz, S.F., et al, *Peptides*, vol. 12, pp. 1251–1260, "Analysis of Neuropeptide Y–Induced Feeding: Dissociation of $Y_1$ and $Y_2$ Receptor Effects on Natural Meal Patterns".

Flood. J.F., et al, *Peptides*, vol. 13, pp. 577–580, 1992, "Differential Effects of Amylin on Memory Processing Using Peripheral and Central Routes of Administration".

Grundemar, L., et al, TiPS, May 1994 [vol. 15], "Neuropeptide Y effector systems: perspectives for drug development".

Stanley, B.G., et al, *Peptides*, vol. 13, pp. 581–587, 1992, "Evidence for Neuropeptide Y Mediation of Eating Produced by Food Deprivation and for a Variant of the $Y_1$ Receptor Mediating This Peptides's Effect".

Sokolova, V. N., et al, S. Ordzhonikidze All–Union Scientific Pharmaceutical Chemistry Research Institute, Moscow. Translated from Khimiko–Farmatsevticheskii Zhurnal, vol. 8, No. 1;pp. 14–17, Jan., 1974. Original article submitted Sep. 29, 1972, "Study of a Pyrrole [3,2–d]Pyrimidine Series. II."

Sokolova, V.N., et al, S. Ordzhonikidze All–Union Scientific–Research Institute of Pharmaceutical Chemistry, Moscow. Translated from Khimiko–Farmatseyticheskii Zhurnal, vol. 7, No. 3, pp. 19–24, Mar. 1973. Original article submitted Sep. 24, 1971. "Study in the Pyrrole(3,2–d)Pyrimidine Series".

Modnikova, G.A., S. Ordzhonikidze All–Union Reasearch Institute for Pharmaceutical Chemistry (VNIKhFI), Moscow. Translated from Khimiko–farmatsevticheskii Zhurnal, vol. 22, No. 2, pp. 185–191, Feb., 1988. Original article submitted Oct. 13, 1986. "Synthesis and Biological Activity of Aminopyrrolo[3,2–d]Pyrimidines".

* cited by examiner

*Primary Examiner*—Mukund J. Shah
*Assistant Examiner*—Ben Schroeder
(74) *Attorney, Agent, or Firm*—Peter C. Richardson; Gregg C. Benson; Mervin E. Brokke

(57) ABSTRACT

This invention provides a means of inhibiting or preventing a disease or condition associated with an excess of neuropeptide Y which comprises administering to a mammal in need of such treatment an effective amount of a compound of the formula:

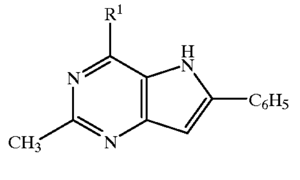

wherein $R^1$ is a nitrogen containing heterocyclic compound.

3 Claims, No Drawings

4-AMINOPYRROLE (3, 2-D) PYRIMIDINES AS NEUROPEPTIDE Y RECEPTOR ANTAGONISTS

CROSS REFERENCE TO RELATED APPLICATIONS

This application is the national stage of International Application No. PCT/IB98/01053, filed Jul. 10, 1998, entitled "4-AMINO PYRROLE (3-2-D) PYRIMIDINES AS NEUROPEPTIDE Y RECEPTOR ANTAGONISTS", which claims priority from U.S. Provisional Application No. 60/054,734, filed Aug. 5, 1997, now abandoned.

BACKGROUND OF INVENTION

1. Field of the Invention

This invention relates to the use of certain substituted 4-aminopyrrole(3,2-d)pyrimidine derivatives which selectively bind to mammalian Neuropeptide receptors. It further relates to the use of such compounds and compositions in treating conditions related to an excess of neuropeptide Y such as feeding disorders and certain cardiovascular diseases.

2. Description of the Related Art

Neuropeptide Y, a peptide first isolated in 1982, is widely distributed in the central and peripheral neurons and is responsible for a multitude of biological effects in the brain and the periphery. Various animal studies have shown that activation of neuropeptide Y1 receptors is related to vasoconstriction, Wahlestedt et al. *Regul. Peptides*, 13: 307–318 (1986), McCauley and Westfall, *J. Pharmacol. Exp. Ther*. 261:863–868 (1992), and Grundemar et al., Br. *J. Pharmacol.* 105:45–50 (1992); and to stimulation of consummatory behavior, Flood and Morley, *Peptides*, 10:963–966 (1989), Leibowitz and Alexander, *Peptides*, 12:1251–1260 (1991), and Stanley et al. *Peptides*, 13:581–587 (1992).

Grundemar and Hakanson. *TiPS*, May 1994 [Vol. 15], 153–159, state that, in animals, neuropeptide Y is a powerful stimulus of food intake, and an inducer of vasoconstriction leading to hypertension. They further point out that low levels of neuropeptide Y (NPY) are associated with loss of appetite. These reports clearly indicate that compounds that inhibit the activity of this protein will reduce hypertension and appetite in animals.

EP0759441 and U.S. Pat. No. 5,576,337 report that physiological disorders related to neuropeptide Y include:

disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia;

conditions related to pain or nociception;

diseases related to abnormal gastrointenstinal motility and secretion, such as different forms of ileus, urinary incontinence, and Crohn's disease;

abnormal drink and food intake disorders, such as anorexia and metabolic disorders; diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

WO 96/14307 describes substituted benzylamine derivatives which selectively bind to human neuropeptide Y1 receptors.

The synthesis of certain 4-aminopyrrole (3,2-d) pyridines is described in *Pharm. Chem J.* 22, 185 (1988); 8, 14 (1974); and 7, 19 (1973). These compounds were reported to have antibacterial and antitumor activity.

SUMMARY OF THE INVENTION

This invention provides a compound of the formula:

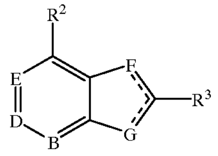

wherein:

B, D and E are independently selected from $CR^1$, $CR^9$ or N with the proviso that at least one of B, D and E must be $CR^1$ or $CR^9$, and at least one of B, D and E must be N; and F and G are selected from N, $NR^4$, or $CR^5$ with the proviso that at least one of F or G must be N or $NR^4$; and one of the dotted lines represents a bond and the other represents no bond; and when B and E are both N, then one of F or G must be $CR^5$; and $R^1$, $R^3$, $R^4$, $R^5$ and $R^9$ are independently selected from H, $(C_1–C_6)$ alkyl, $(C_1–C_6)$ alkoxy, $(C_1–C_6)$ thioalkyl, $(C_2–C_6)$ alkenyl, $(C_2–C_6)$ alkynyl, $(C_1–C_6)$ perfluoroalkyl, $(C_1–C_6)$ perfluoroalkoxy, $(CH_2)_n$—$(C_3–C_7)$ cycloalkyl, $(CH_2)_n(C_3–C_7)$ cycloalkenyl, and $(CH_2)_n$ Ar, wherein each alkyl, alkenyl, alkynyl, alicyclic and Ar group may be independently substituted with one to three substituents selected from the group consisting of Br, Cl, F, $NR^6R^7$, $O(C_1–C_6)$ alkyl, $NO_2$, CN, COOH, OH, SH and;

$R^2$ is $NR^6R^7$,

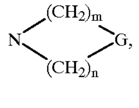

$NH(CH_2)_n$ Ph, $NH(CH_2)_n(C_3–C_7)$ cycloalkyl, $NH(CH_2)_n$, $(C_3–C_7)$ cycloalkenyl, $NH(CH_2)_n$ morpholinyl, $NH(CH_2)_n$ piperazinyl, or $NH(CH_2)_n$ pyrimidinyl wherein each ring may be independently substituted with one to three substituents selected from the group consisting of Br, Cl, F, $NR^6R^7$, $O(C_1–C_6)$ alkyl, $(C_1–C_6)$ alkyl, $S(O)_m$ $(C_1–C_6)$ alkyl, $NO_2$, CN, COOH, OH, and SH and;

$R^2$ is $OR^1$, 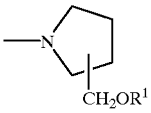 , 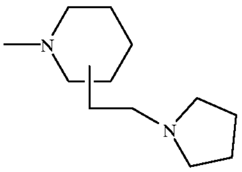 ,

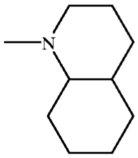 , 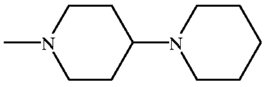 ,

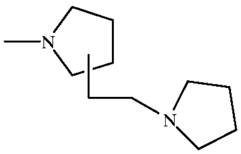 , and 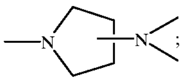 ; and when $R^2$ is

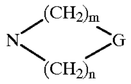

if m or n is zero the other of m or n must be at least 2; and

G is S, O, $NR^8$ or a bond; and $R^8$ is hydrogen, $(C_1–C_6)$ alkyl or aryl; $(C_1–C_6)$ alkyl

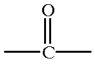

or

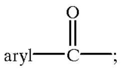

$R^6$ and $R^7$ are independently selected from hydrogen, $(C_1–C_6)$-alkyl, $(C_1–C_6)$ alkyl $(C_1–C_6)$ alkoxy, $(CH_2)_k$ $N[(C_1–C_6)\ alkyl]_2$ and $(CH_2)_k$ OH; and n is and integer from zero to six;

m is an integer from zero to two;

k is an integer from two to four;

Ar is an aromatic hydrocarbon or a heterocyclic ring of three to seven atoms or a bicyclic heterocyclic ring at least atom one of which is a nitrogen, sulfur or oxygen atom;

and with the proviso that if F is $NR^4$, G is $CR^5$, B and E are N; D is $CR^1$; $R^1$ is methyl, $R^3$ is phenyl and $R^4$ and $R^5$ are hydrogen then $R^2$ must not be $NEt_2$, $HN(CH_2)_2\ NEt_2$, $HN(CH_3)_2\ COOH$, $HNCH_2CH_2OH$, HNPh, $HN(CH_2)_2Ph$,

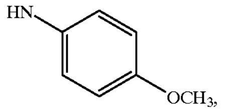 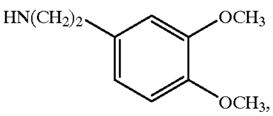

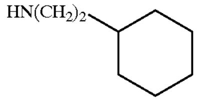 , 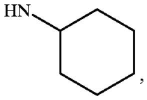 , piperidinyl, morpholinyl, $NHNH_2$, $HNCH(CH_3)_2$, $HN(CH_2)_3\ CH_3$, $HNCH_2CH(CH_3)_2$, $HNCH(CH_3)CH_2(CH_2)_3CH3$, $HNCH_2CH{=}CH_2$,

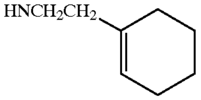 , $HN\ CH_2C_6H_5$ or , 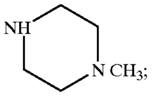

and with the further proviso that if F is $NR^4$, G is $CR^5$, B and E are N; D is $CR^1$; R1 and $R^3$ are both methyl and $R^4$ and $R^5$ are both hydrogen then $R^2$ must not be $HNCH_2CH_2N(C_2H_5)_2$, 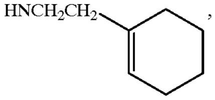 , $HNCH_2C_6H_5$, $HN(CH_2)_2C_6H_5$, 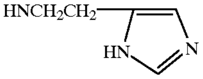 ,

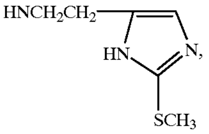 or 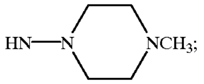

and with the further proviso that if F is $NR^4$, G is $CR^5$, B and E are N; D is $CR^1$; R3, $R^4$ and $R^5$ are hydrogen then $R^1$ and $R^2$ must not both be the same and be

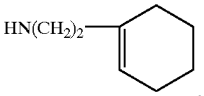 , 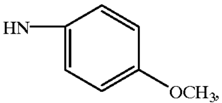 $N(CH_3)_2$ or HNPh.

and with the further proviso that when B,F are N; G is $NR^4$; D is $CR^1$; E is $CR^9$; $R^1$, $R^3$, and $R^4$ are H then R2 must not be $NH_2$, $NMe_2$, NHMe, OH, OMe,

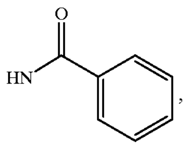 , 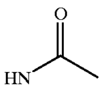 , 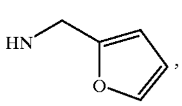 ,

-continued

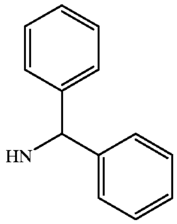

; and when B and G are N; F is $NR^4$; E is $CR^9$; D is $CR^1$; $R^1$, $R^4$, and $R^9$ are H; and $R^2$ is OMe, then $R^3$ must not be

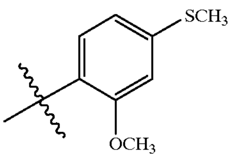

or

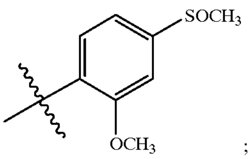

; and when B and G are N; F is $NR^4$; E is $CR^9$; D is $CR^1$; $R^1$, $R^3$, and $R^9$ are H; and $R^2$ is $NH_2$ then $R^4$ must not be

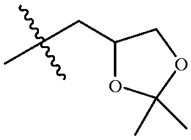

,

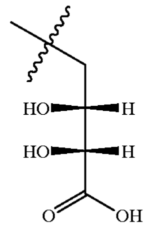

,

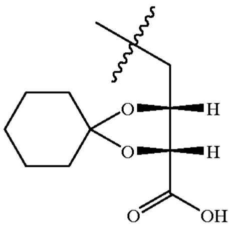

; and when B and F are N; G is $NR^4$; E is $CR^9$; D is $CR^1$; $R^1$ and $R^9$ are H; $R^3$ and $R^4$ are $CH_3$ then $R^2$ must not be

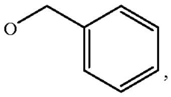

,

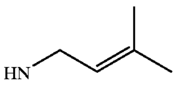

,

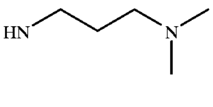

,

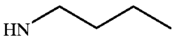

,

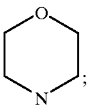

; and when B and F are N; G is $NR^4$; E is $CR^9$; D is $CR^1$; $R^1$ and $R^9$ are H; $R^3$ is $CH_3$ and R4 is $CH_2CH_2OH$ then $R^2$ must not be $NH_2$ or

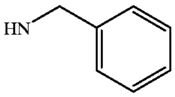

; and when B and F are N; G is $NR^4$; E is $CR^9$; D is $CR^1$; $R^1$ is $CH_3$; $R^3$ is $CH_3$; $R^9$ is H and $R^4$ is

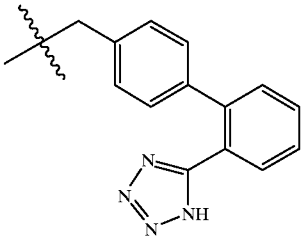

then $R^2$ must not be $NMe_2$, NHMe, or

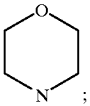

; and when E and F are N; G is $NR^4$; B is $CR^9$; D is $CR^1$; $R^1$; $R^3$; $R^4$ and $R^9$ are H then $R^2$ must not be $NH_2$, OH, $OCH_3$, $NMe_2$, NHEt, NHMe,

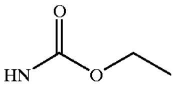

,

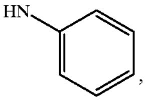

,

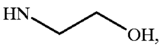

,

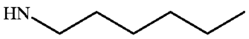

,

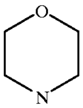

,

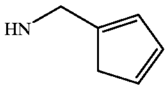

; and when E and F are N; G is $NR^4$; B is $CR^9$; D is $CR^1$; $R^1$ is $CH_3$; and $R^3$, $R^4$; and $R^9$ are H then $R^2$ must not be $NH_2$ or OH; and when E and F are N; G is $NR^4$; B is $CR^9$; D is $CR^1$; $R^1$ is $CH_2CH_2CH_3$; and $R^3$, $R^4$; and $R^9$ are H then $R^2$ must not be $NH_2$ or OH; and when E and F are N; G is $NR^4$; B is $CR^9$; D is $CR^1$; $R^1$, $R^4$; and $R^9$ are H and $R^2$ is $OCH_3$ then $R^3$ must not be

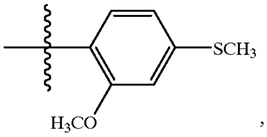

,

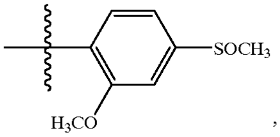

,

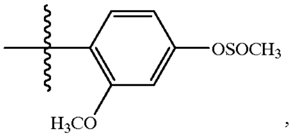

,

-continued

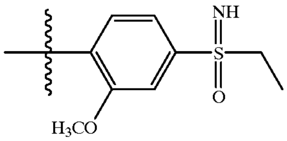

.

When E and G are N; F is $NR^4$; B is $CR^9$; D is $CR^1$; $R^2$ is $NH_2$; $R^1$, $R^3$; and $R^9$ are H then $R^4$ must not be $CH_3$ or

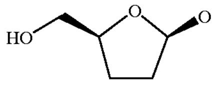
,
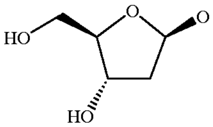
,
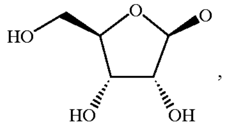
,
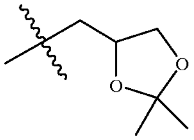
,
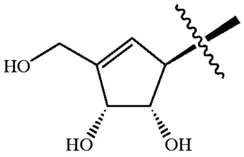
,
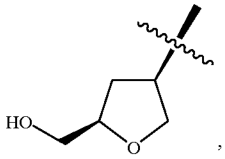
,
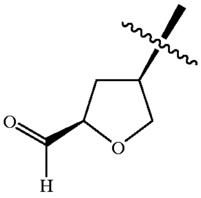
,
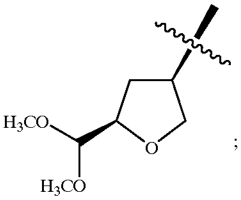
; and when E and F are N; G is $NR^4$; B is $CR^9$; D is $CR^1$; $R^2$ is OH; $R^1$, $R^4$; and $R^9$ are H then $R^3$ must not be $CH_3$, Et, or

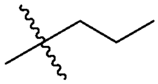
,
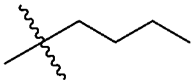
,
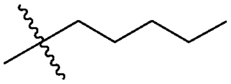
,
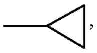
,
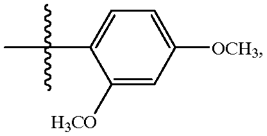
,
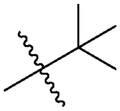
,
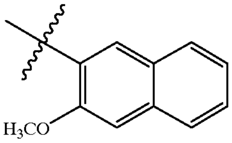
,
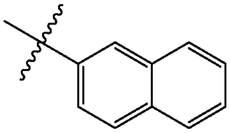
, -continued

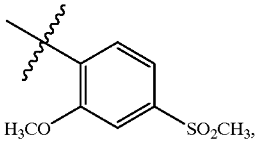
,
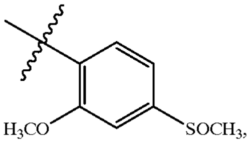
,
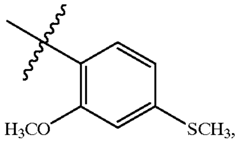
,
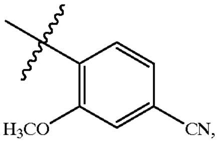
,
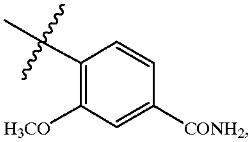
,
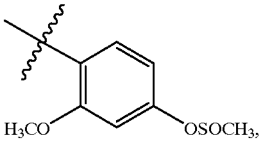
,
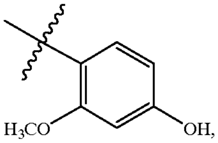
,
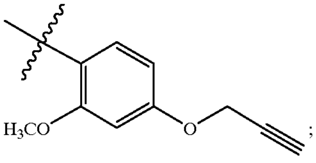
;

and when E and G are N; F is $NR^4$; B is $CR^9$; D is $CR^1$; $R^2$ is OH; $R^1$ and $R^9$ are H and $R^4$ is

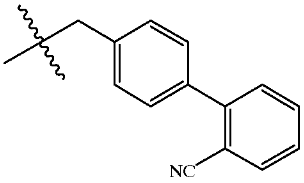

then $R^3$ must not be Et, cyclopropyl, propyl, or butyl; and when E and G are N; F is $NR^4$; B is $CR^9$; D is $CR^1$; $R^2$ is OH; $R^1$ and $R^9$ are H and $R^4$ is

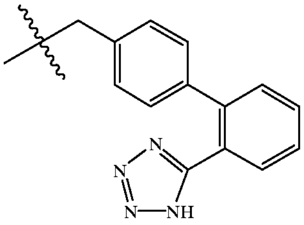

then $R^3$ must not be Et, cyclopropyl, propyl, or butyl; and when E and G are N; F is $NR^4$; B is $CR^9$; D is $CR^1$; $R^2$ is OH; $R^1$ and $R^9$ are H and $R^3$ is $CH_2CH_2CH_2CH_3$ then $R^4$ must not be -continued
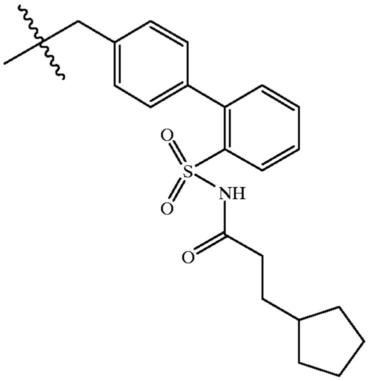
,
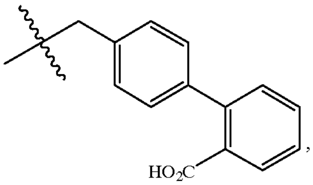
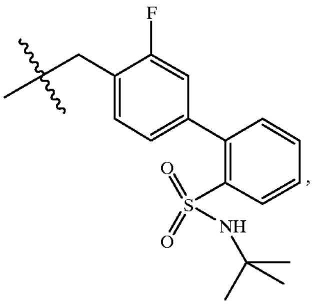
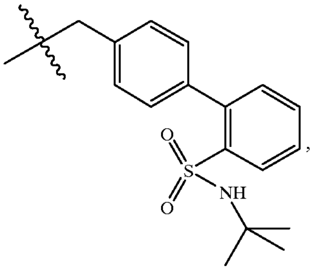
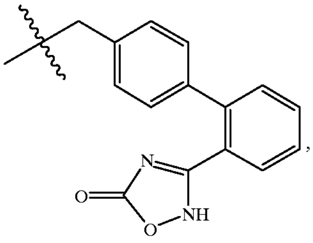
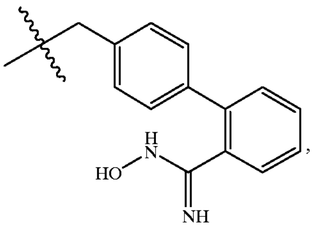
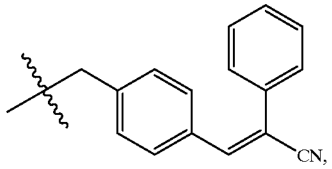
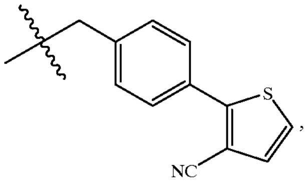
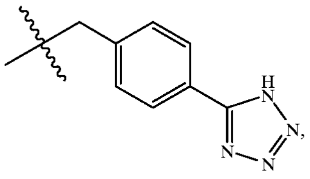
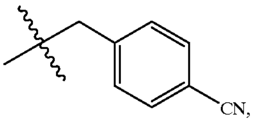
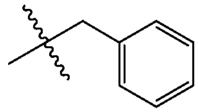
,
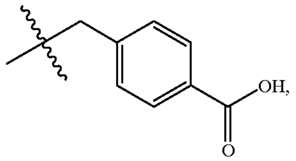
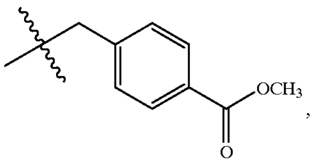
,
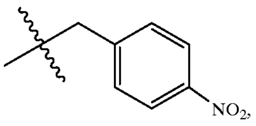
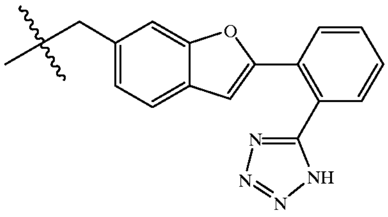
,
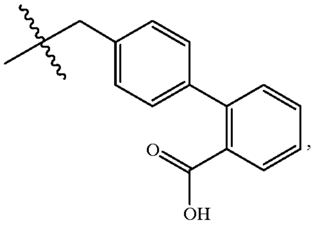
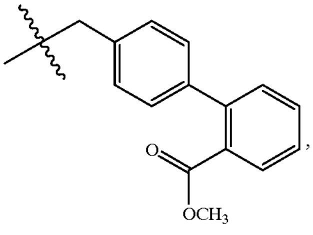

-continued

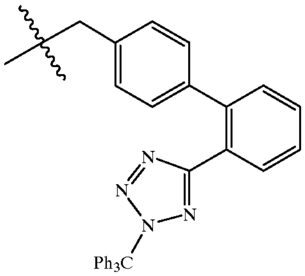

;

and when E and F are N; G is $NR^4$; B is $CR^9$; D is $CR^1$; and $R^1$, $R^4$ and $R^9$ are H and $R^3$ is 2,4-dimethoxyphenyl then $R^2$ must not be

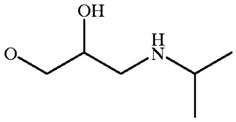

,

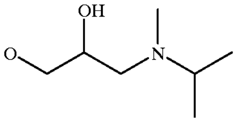

,

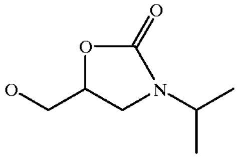

;

and when E and G are N; F is $NR^4$; B is $CR^6$; D is $CR^1$; $R^1$ and $R^9$ are H; $R^2$ is OH and $R^3$ is $CH_2CH_2CH_3$ then $R^4$ must not be

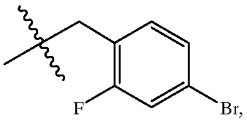

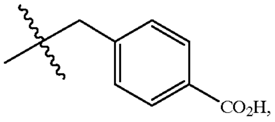

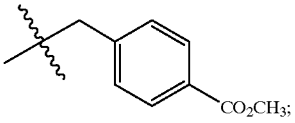

and when E and F are N; G is $NR^4$; B is $CR^9$; D is $CR^1$; $R^1$ and $R^9$ are H; $R^2$ is $N(CH_2C_6H_5)_2$ and $R^3$ is $CH_3$ then $R^4$ must not be $CH_2CH_2C_6H_5$ or $CH_2CH_2CH_2CH_3$; and when E and F are N; G is $NR^4$; B is $CR^9$; D is $CR^1$; $R^1$ and $R^9$ are H; $R^2$ is $N(CH_2C_6H_5)_2$ and $R^4$ is $CH(CH_3)CH_2CH_3$ then $R^3$ must not be

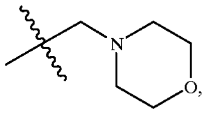

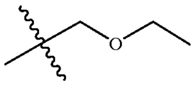

,

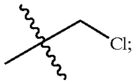

and when E and F are N; G is $NR^4$; B is $CR^9$; D is $CR^1$; $R^1$ and $R^9$ are H; $R^2$ is $NH_2$ and $R^3$ is $CH_3$ then $R^4$ must not be

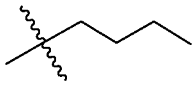

,

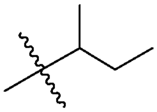

,

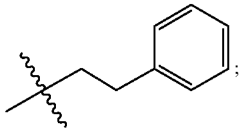

;

and when E and F are N; G is $NR^4$; B is $CR^9$; D is $CR^1$; $R^1$ and $R^9$ are H; $R^2$ is $NH_2$ and $R^4$ is $CH(CH_3)CH_2CH_3$ then $R^3$ must not be

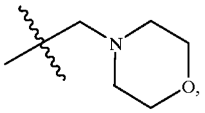

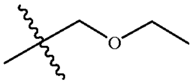

,

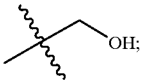

and the following compounds are not included in the invention;

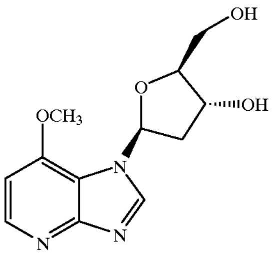

-continued
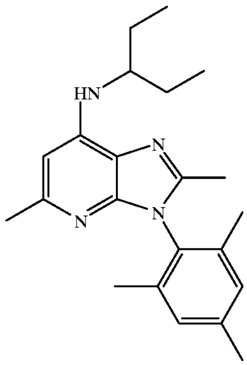
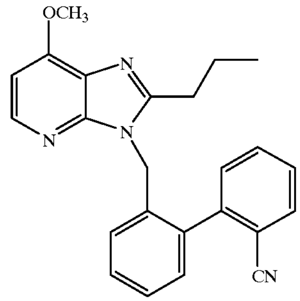
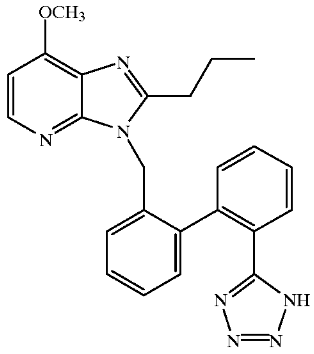
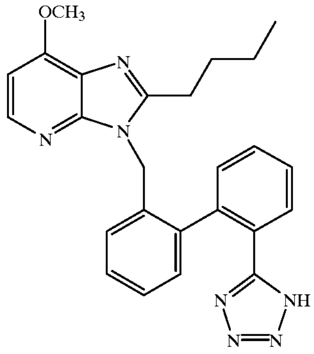
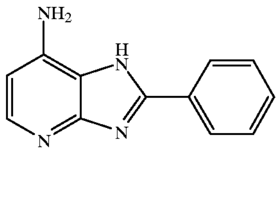
-continued
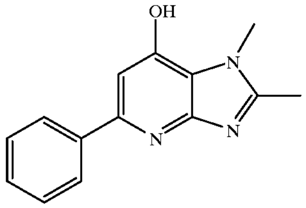
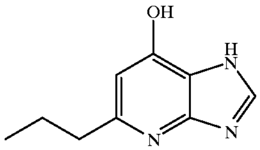
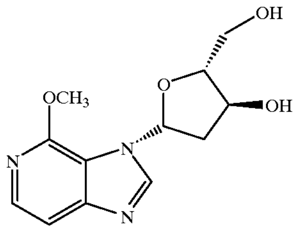
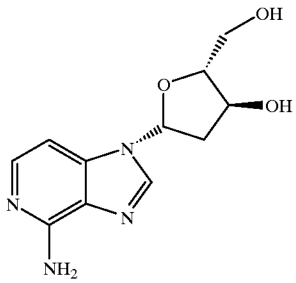
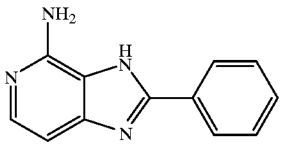
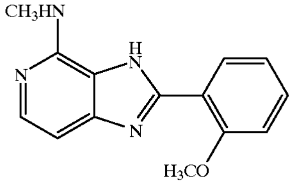
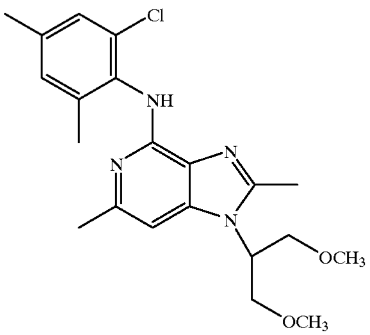

-continued

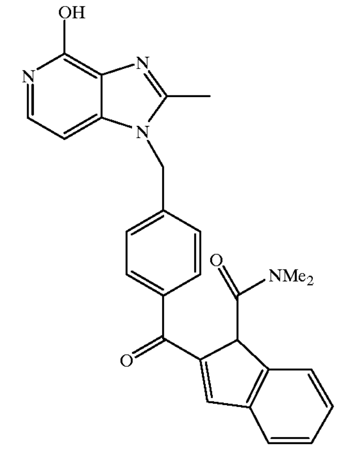

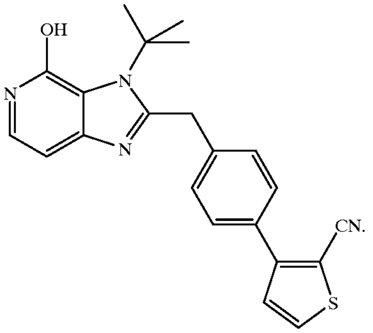

This invention also provides a compound of the formula:

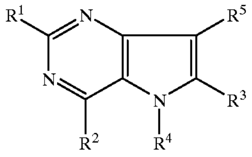

wherein:

$R^1$, $R^3$, $R^4$, and $R^5$ are independently selected from H, $(C_1-C_6)$ alkyl, $(C_1-C_6)$ alkoxy, $(C_1-C_6)$ thioalkyl, $(C_2-C_6)$ alkenyl, $(C_2-C_6)$ alkynyl, $(C_1-C_6)$ perfluoroalkyl, $(C_1-C_6)$ perfluoroalkoxy, $(CH_2)_n$ phenyl, $(CH_2)_n$ pyridyl, $(CH_2)_n$ pyrimidyl, $(CH_2)_n$ $(C_3-C_7)$ cycloalkyl, $(CH_2)_n$ $(C_3-C_7)$ cycloalkenyl, $(CH_2)_n$ furanyl, $(CH_2)_n$ thienyl wherein each alkyl, alkenyl, alkynyl, phenyl, heterocyclic and alicyclic group may be independently substituted with one to three substituents selected from the group consisting of Br, Cl, F, $NR^6R^7$, $O(C_1-C_6)$ alkyl, $(C_1-C_6)$ alkyl, $S(O)_m$ $(C_1-C_6)$ alkyl, $NO_2$, CN, COOH, OH, SH and;

$R_2$ is $NR^6R^7$,

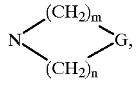

$NH(CH_2)_n$ Ph, $NH(CH_2)_n$ $(C_3-C_7)$ cycloalkyl, $NH(CH_2)_n$ $C_3-C_7)$ cycloalkenyl, $NH(CH_2)_n$ morpholinyl, $NH(CH_2)_n$ piperazinyl, or $NH(CH_2)_n$ pyrimidinyl wherein each ring may be independently substituted with one to three substituents selected from the group consisting of Br, Cl, F, $NR^6R^7$, $O(C_1-C_6)$ alkyl, $(C_1-C_6)$ alkyl, $S(O)_m$ $(C_1-C_6)$ alkyl, $NO_2$, CN, COOH, OH, and SH and;

when $R_2$ is

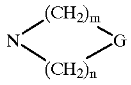

if m or n is zero the other of m or n must be at least 2; and

G is S, O $NR^8$ or a bond; and $R^8$ is hydrogen, $(C_1-C_6)$ alkyl or aryl; and $R^6$ and $R^7$ are independently selected from hydrogen, $(C_1-C_6)$ alkyl $(C_1-C_6)$ alkoxy, $(CH_2)_k$ $N[(C_1-C_6)$ alkyl$]_2$ and $(CH_2)_k$ OH; and n is an integer from zero to six;

m is an interger from zero to two;

k is an integer from two to four; and pharmaceutically acceptable salts thereof;

and with the proviso that if $R^1$ is methyl, $R^3$ is phenyl and $R^4$ and $R^5$ are hydrogen then $R^2$ must not be $NET_2$, $HN(CH_2)_2$ $NET_2$, $HN(CH_3)_2$ COOH, $HNCH_2CH_2OH$, HNPh, $HN(CH_2)_2Ph$,

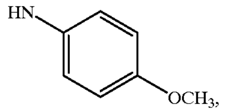

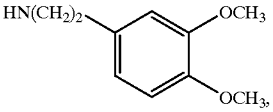

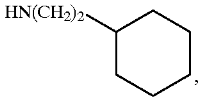,

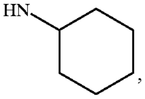, piperidinyl, morpholinyl, $NHNH_2$, $HNCH(CH_3)_2$, $HN(CH_2)_3$ $CH_3$, $HNCH_2CH(CH_3)_2$, $HNCH(CH_3)CH_2$ $(CH_2)_3CH3$, $HNCH_2CH{=}CH_2$,

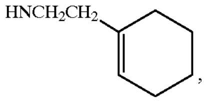, $HN\ CH_2C_6H_5$ or, 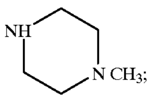

and with the further proviso that if $R_1$ and $R_3$ are both methyl and $R^4$ and $R^5$ are both hydrogen then $R^2$ must not be $HNCH_2CH_2N(C_2H_5)_2$, 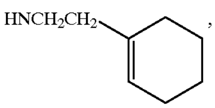, $HNCH_2C_6H_5$, $HN(CH_2)_2C_6H_5$, 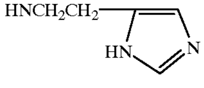,

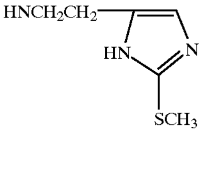, or 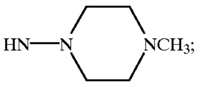

and with the further proviso that if $R^3$, $R^4$ and $R^5$ are hydrogen then $R^1$ and $R^2$ must not both be the same and be

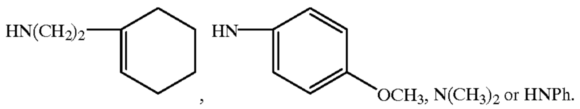

In another aspect, this invention provides a compound selected from the group consisting of:

2-Methyl-4-isopropylamino-6-phenylpyrrolo[3,2-d] pyrimidine;

6-Methyl-2-phenyl-4-pyrrolidin-1-yl-1H-imidazo[4,5-c] pyridine;

5-Methyl-7-pyrrolidin-1-yl-2-thiazol-2-yl-3H-imidazo[4,5-b]pyridine;

2-(1H-Imidazol-2-yl)-5-methyl-7-pyrrolidin-1-yl-3H-imidazo[4,5-b]pyridine;

2-Cyclohexyl-5-methyl-7-pyrrolidin-1-yl-3H-imidazo[4,5-b]pyridine;

2-(2,4-Dimethoxy-phenyl)-7-methoxy-5-methyl-3H-imidazo[4,5-b]pyridine;

7-Methoxy-5-methyl-2-phenyl-3H-imidazo[4,5-b] pyridine;

5-Methyl-2-pyridin-4-yl-7-pyrrolidin-1-yl-3H-imidazo [4,5-b]pyridine;

5-Methyl-2-pyridin-3-yl-7-pyrrolidin-1-yl-3H-imidazo [4,5-b]pyridine;

5-Methyl-2-pyridin-2-yl-7-pyrrolidin-1-yl-3H-imidazo [4,5-b]pyridine;

2-(4-Fluoro-phenyl)-5-methyl-7-piperidin-1-yl-3H-imidazo[4,5-b]pyridine;

(S)-4-(2-Methoxymethyl-pyrrolidin-1-yl)-2-methyl-6-phenyl-5H-pyrrolo[3,2d]pyrimidine;

(RS)-2-Methyl-6-phenyl-4-[2-(2-pyrrolidin-1-yl-ethyl)-piperidin-1-yl]-5H-pyrrolo[3,2-d]pyrimidine;

5-Methyl-2-phenyl-7-pyrrolidin-1-yl-1H-imidazo[4,5-b] pyridine;

5-Methyl-2-phenyl-7-piperidin-1-yl-1H-imidazo[4,5-b] pyridine;

1-(2-Methyl-6-phenyl-5H-pyrrolo[3,2-d]pyrimidin-4-yl)-decahydro-quinoline;

1'-(2-Methyl-6-phenyl-5H-pyrrolo[3,2-d]pyrimidin-4-yl)-[1,4']bipiperidinyl;

(R)-4-(2-Methoxymethyl-pyrrolidin-1-yl)-2-methyl-6-phenyl-5H-pyrrolo[3,2d]pyrimidine;

(S)-2-Methyl-6-phenyl-4-(2-pyrrolidin-1-ylmethyl-pyrrolidin-1-yl)-5H-pyrrolo[3,2-d]pyrimidine; and (R)-Dimethyl-[1-(2-methyl-6-phenyl-5H-pyrrolo[3,2-d] pyrimidin-4-yl)-pyrrolidin-3-yl]-amine.

In another aspect this invention provides a compound of the structure:

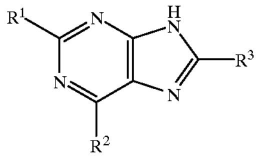

wherein $R^1$ is $C_1$–$C_6$ alkyl, $R^3$ is Ar and $R^2$; $R^2$, $R^3$ and Ar have the meanings described above.

In another aspect this invention provides a method of inhibiting or alleviating a pathological condition or physiological disorder in a mammalian subject characterized by or associated with an excess of neuropeptide Y which comprises administering to said subject an effective amount of a compound of Formula I.

The compounds of this invention are basic in nature and are capable of forming a wide variety of salts with various inorganic and organic acids. The acids that may be used to prepare pharmaceutically acceptable acid addition salts of those compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, saticylate, citrate, acid citrate, tartrate, pantothenate, bitartrate, ascorbate, succinate, maleate, fumarate, gluconate, glucaronate, saccharate, formate, benzoate, glutamate, methanesulfonate, ethanesulfonate, benzenesulfonate, and p-toluenesulfonate.

Compounds that interact with NPY receptors and inhibit the activity of neuropeptide Y at those receptors are useful in treating numerous disorders associated with neuropeptide Y. This invention therefore provides a method of using compounds of Formula I which selectively bind to neuropeptide Y receptors and are useful in treating feeding disorders such as obesity and bulimia as well as disorders or diseases pertaining to the heart, blood vessels or the renal system, such as vasospasm, heart failure, shock, cardiac hypertrophy, increased blood pressure, angina, myocardial infarction, sudden cardiac death, arrythmia, peripheral vascular disease, and abnormal renal conditions such as impaired flow of fluid, abnormal mass transport, or renal failure; conditions related to increased sympathetic nerve activity for example, during or after coronary artery surgery, and operations and surgery in the gastrointestinal tract; cerebral diseases and diseases related to the central nervous system, such as cerebral infarction, neurodegeneration, epilepsy, stroke, and conditions related to stroke, cerebral vasospasm and hemmorrhage, depression, anxiety, schizophrenia, and dementia; conditions related to pain or nociception; diseases related to abnormal gastrointenstinal motility and secretion, such as different forms of ileus, urinary incontinence, and Crohn's disease; abnormal drink and food intake disorders, such as anorexia and metabolic disorders; diseases related to sexual dysfunction and reproductive disorders; conditions or disorders associated with inflammation; respiratory diseases, such as asthma and conditions related to asthma and bronchoconstriction; and diseases related to abnormal hormone release, such as leutinizing hormone, growth hormone, insulin, and prolactin.

This invention also relates to a pharmaceutical composition comprising a compound of the invention or a pharmaceutically acceptable salt thereof and a pharmaceutically acceptable carrier.

This invention also relates to compositions useful for treating obesity and related conditions which comprise effective amounts of a compound of this invention and a $B_3$-adrenergic agent or a thyromimetic agent.

A preferred $B_3$ adrenergic agent is (4-(2-(2-(6-aminopyridin-3-yl)-2(R)-hydroxyethylamino)ethoxy) phenyl)acetic acid and its salts and prodrugs.

DETAILED DESCRIPTION OF THE INVENTION

Compounds of Formula I are prepared by methods which are known in the chemical literature. Compounds may be prepared by the general methods of Sokolova, et al. *Pharm. Chem. J.*, 8, 14 (1974) and *ibid*, 7, 19 (1973) or Modnikova, et al. *Pharm. Chem. J.*, 22 185 (1988). The above references are incorporated herein by reference.

Compounds of the invention may be prepared by the following reaction sequence.

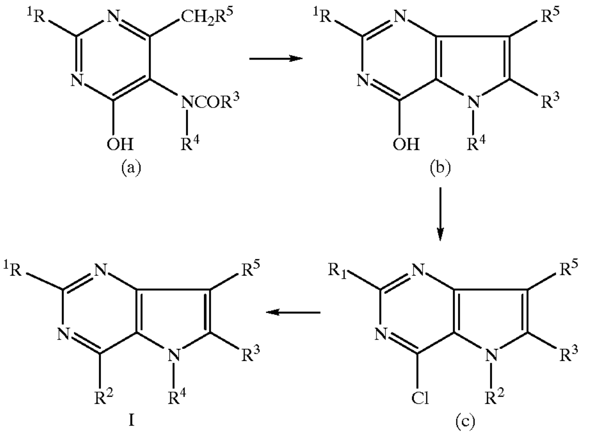

(a) (b) (c) I

Compounds (a) and (b) may also be prepared by the procedures described in *Chem. Pharm. Bull.* (Tokyo) 12, 1024 (1964) and *J. Am. Chem. Soc.* 74, 4897 (1952) or other standard synthetic procedures. The chemist of ordinary skill will recognize that changes in reaction conditions may be necessary when different R-groups are present. For example, protecting groups may be required when one of the R-groups contains an additional functionality. Compound (c) is conveniently prepared from compound (b) with a chlorinating agent such as phosphorous oxychloride.

Compounds of the invention may be prepared by the following reaction sequence.

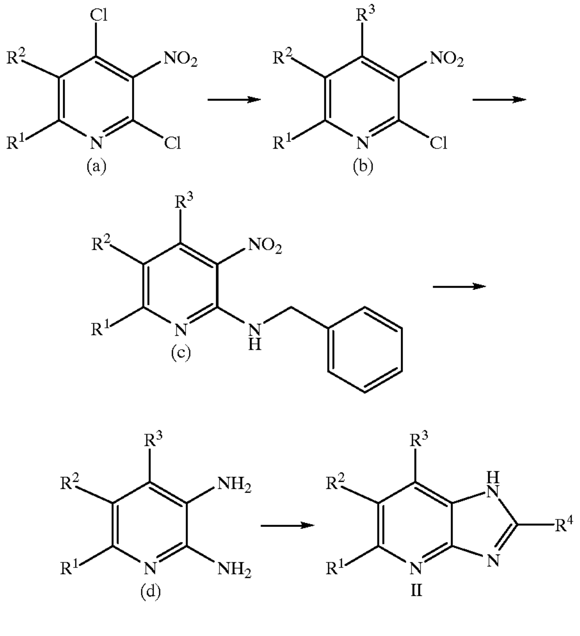

(a) (b) (c) (d) II

The pharmaceutical utility of compounds of this invention is indicated by the following assay for human NPY1 receptor activity.

Assay for-Human NPY1 Receptor Binding Activity

The procedure used is similar to that described by Gordon et al. (*J. Neurochem.* 55:506–513, 1990). SK-N-MC cells were purchased from ATCC (Rockville, Md.). Cells were maintained at 37° C. and 5% $CO_2$ in Dulbecco's modified essential media (DMEM) with L-glutamine and 110 mg/L sodium pyruvate, which was supplemented with 10% fetal bovine serum and 25 mM HEPES (pH 7.3). The binding assay was performed in 24-well plates (Falcon) when the cells were confluent. Taking care to not disturb the cells on the bottom of the wells, the media was aspirated, and 0.5 ml of Dulbecco's phosphate buffered saline (DPBS) with calcium and magnesium were added to each well. The DPBS was aspirated and an additional aliquot of DPBS was added and aspirated. To begin the assay, binding buffer consisting of serum-free DMEM containing 0.5% bovine serum albumin, 0.1% bacitracin and 0.1 mM phenylmethylsulfonylfluoride was added to each well. The cells and the binding buffer preincubated for 30 minutes at room temperature, at which point the drug dilution and [$^{125}$ I]PYY (NEN-DuPont: 50000–75000 cpm ~50 pM) were added to yield a final volume of 250 ul. Nonspecific binding was defined with 1 mM NPY (porcine or human, Bachem Calif.). After a 3 hour incubation at room temperature, the plates were then put on ice and the wells were aspirated. The cells were washed 4–6 times with 0.5 ml of ice-cold DPBS. A dilute solution of Triton X-100 (1%) was then added to each well. After approximately 1 hour at room temperature, an aliquot from each well was transferred to a 12x75 mm test tube, and the amount of [$^{125}$ 1] was quantitated on a gamma counter with an efficiency of 80–85% (Genesys 5000, Laboratory Technologies). $IC_{50}$ values were calculated with the non-linear curve fitting program RS/1 (BBN Software Products Corp., Cambridge, Mass.).

[$^{125}$ I]PYY Binding at Human NPY Receptors Expressed in Sf9 Cells

Baculovirus-infected Sf9 cells expressing recombinant human H17 subtype of NPY receptors are harvested at 48 hours. At the time of harvest, cell pellets are resuspended in lysis buffer (20 mM Tris-HCl, pH 7.4, 5 mM EDTA, 0.5 μg/ml leupeptin, 2 μg/ml Aprotonin and 200 μM PMSF) and homogenized using a Polytron (setting 3, 25–30 seconds). Homogenates are centrifuged at 4° C. for 5 minutes at 200xg (~1500 rpm) to pellet the nuclei. The supematant is collected into a fresh tube and centrifuged at 48,000xg for 10 minutes. Pellets are washed once in lysis buffer and centrifuged. The final pellet is resuspended in PBS and stored in aliquots at −80° C. Purified membranes are washed using PBS and resuspended in binding buffer (50 mM Tris-HCl, pH 7.4, 5 mM KCl, 120 mM NaCl, 2 mM $CaCl_2$, 1 mM $MgCl_2$, 0.1% bovine serum albumin (BSA)). Membranes (20 μg/reaction tube) are added to polypropylene tubes containing 0.030 nM [$^{125}$ I]PYY(porcine), displacers ranging from $10^{-12}$ M to $10^{-5}$ M, and buffer to yield a final volume of 0.250 mL. Nonspecific binding is determined in the presence of 1 $\mu$M NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mLs cold binding buffer without BSA. A gamma counter is used to count filters with an efficiency of 85%. $IC_{50}$ values were calculated with the non-linear curve fitting program RS/1 (BBN Software Products Corp., Cambridge, Mass.).

Functional Assay for NPY Receptors Expressed in Oocytes

Experiments were performed on Xenopus oocytes. Oocytes were prepared and maintained using standard protocols (Dascal and Lotan, in *Methods in Molecular Biology; Protocols in Molecular Neurobiology*, eds. Longstaff & Revest, Humana, Clifton, N.J., 13: 1992). For the present experiments, oocytes were obtained from 6 frogs. Oocytes were recorded from 2–7 days following coinjection of GIRKI and the H17 NPY-1 or NPY-5 subtype mRNA (25 ng of each, 50 nL total volume).

Two electrode voltage clamp recordings were carried out using a Warner Instruments Oocyte clamp OC 725B. Data were collected on a Macintosh microcomputer and analyzed using Superscope software. Voltage and current electrodes were pulled from glass tubing (1.5 mM O.D.) on a Brown/Flaming micropipet puller (Sutter Instruments, model P-87). Electrodes contained 3M KCl and had resistances of 0.5–2 MOhms. Oocytes were bathed in normal external solution containing; 90 mM NaCl, 1 mM KCl, 1 mM $MgCl_2$, 1 mM $CaCl_2$, 5 mM HEPES, pH=7.4. Before NPY agonists or antagonists were introduced, a high $K^+$, solution containing; 1 mM NaCl, 90 mM KCl, 1 mM $MgCl_2$, 1 mM $CaCl_2$, 5 mM HEPES was applied to permit recording of the inwardly rectifying $K^+$ current. Drugs were applied diluted in the high $K^+$ media.

100 $\mu$M stocks of NPY, PP or NPY peptide fragments or PYY peptide fragments were prepared in water and frozen until needed.

Oocytes were voltage-clamped at −80 mV with two electrodes. Oocytes were initially superfused with normal external medium (approximate flow rate 4 ml/min.). Before drugs were applied, cells were superfused with high $K^+$ solution to permit activation of the inwardly rectifying $K^+$ current. In oocytes coinjected with NPY receptor and GIRK1 mRNA, NPY agonists induced an additional inward current over the resting $K^+$ current caused by high $K^+$ medium. Because responses desensitized at slow, but varying rates, cumulative dose applications were administered to generate concentration response curves. Two to four doses of agonists were applied to each cell. Agonist dose responses in each cell were normalized against the response to a maximal concentration of human NPY. Dose response curves were fit with a logistic equation using Kaleidagraph software (Abelbeck software, Reading, Pa.).

The compounds of this invention and pharmaceutically acceptable salts thereof (the active compounds) may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more active compounds may be present in association with one or more non-toxic pharmaceutically acceptable carriers and/or diluents and/or adjuvants and if desired other active ingredients. The pharmaceutical compositions containing active compounds may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The active compounds may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Active compounds may be administered parenterally in a sterile medium, The drug, depending on the vehicle and concentration used can either be suspended or dissolved in the vehicle. Advantageously, adjuvants such as local anesthetics, preservatives and buffering agents can be dissolved in the vehicle.

Dosage levels of the order of from about 0.1 mg to about 15 mg of active compound per kilogram of body weight per day are useful in the treatment of the above-indicated conditions (about 0.5 mg to about 7 g per patient per day). The amount of active compound that may be combined with the carrier materials to produce a single dosage form will vary depending upon the host treated and the particular mode of administration. Dosage unit forms will generally contain between from about 1 mg to about 500 mg of an active compound.

It will be understood, however, that the specific dose level for any particular patient will depend upon a variety of factors including the activity of the specific compound employed, the age, body weight, general health, sex, diet, time of administration, route of administration and rate of excretion, drug combination and the severity of the particular disease undergoing therapy.

This invention also relates to compositions useful for treating obesity and related conditions which comprise effective amounts of a compound of this invention and a $B_3$—adrenergic agent or a thyromimetic agent.

(4-(2-(2-(6-Aminopyridin-3-yl)-2(R)-hydroxyethylamino)ethoxy)acetic acid is disclosed in commonly assigned International Patent Application Publication Number WO 96/35671, the disclosure of which is incorporated herein by reference, as a β-adrenergic agent. Accordingly, (4-(2-(2-(6-aminopyridin-3-yl)-2(R)-hydroxyethylamino)ethoxy)acetic acid has utility in the treatment of obesity.

β-Adrenergic agents have been categorized into $\beta_1$, $\beta_2$, and $\beta_3$ subtypes. Agonists of β-receptors promote the activation of adenyl cyclase. Activation of $\beta_2$ receptors induces relaxation of smooth muscle tissue which produces a drop of blood pressure and the onset of skeletal muscle tremors. Activation of $\beta_3$ receptors is known to stimulate lipolysis, which is the breakdown of adipose tissue triglycerides to glycerol and fatty acids. Activation of $\beta_3$ receptors also stimulates the metabolic rate, thereby increasing energy expenditure. Accordingly, activation of $\beta_3$ receptors promotes the loss of fat mass. Compounds that stimulate β receptors and therefore useful as anti-obesity agents.

Certain thyromimetic compounds have been disclosed having the ability to induce weight loss by mechanisms other than appetite suppression, e.g. through stimulation of the peripheral metabolic rate of adipose tissue. For example, U.S. Pat. Nos. 4,451,465, 4,772,631, 4,977,148, 4,999,377 and 5,284,971 disclose compounds possessing thermogenic properties at dosages causing little or no side-effects, such as cardiac stimulation. The disclosures of U.S. Pat. Nos. 4,451, 465, 4,772,631, 4,977, 148, 4,999,377 and 5,284,971 are incorporated herein by reference in their entirety. It is well-known to one skilled in the art that selectivity of thermogenic effect is an important requirement for a useful therapeutic agent in the treatment of, for example, obesity and related conditions.

When treating obesity, generally satisfactory results are obtained when the combination of the instant invention, i.e., a compound of this invention in combination with (4-(2-(2-(6-aminopyridil-3-yl)-2(R)-hydroxyethylamino)ethoxy) phenyl)acetic acid, prodrugs, or pharmaceutically acceptabe salts thereof (hereinafter also referred to herein as "active ingredients or compounds") are administered to animals, including humans, via either the oral or the parenteral route. Administration by the oral route is preferred, being more convenient and avoiding the possible pain and irritation of injection. However, in circumstances where the subject cannot swallow the medication, or absorption following oral administration is impaired, as by disease or other abnormality, it is essential that the drug be administered parenterally. By either route, the dosage of the compound of Formula I is in the range of about 0.01 to about 50 mg/kg/day body weight of the subject per day, preferably about 0.3 to about 30 mg/kg/day body weight per day, and most preferably about 1 to about 10 mg/kg/day body weight, administered singly or as a divided dose. The dosage of the compound which modifies eating behavior is in the range of about 0.01 to about 15 mg/kg/day body weight, preferably about 0.1 mg/kg/day to about 10 mg/kg/day body weight, administered singly or as a divided dose.

As a consequence of their action in treating pathological conditions the compounds of the present invention possess utility for treatment of ungulate animals such as swine, cattle, sheep, and goats. Active compounds of the invention can additionally be used for the treatment of household pets, for example companion animals such as dogs and cats. The administration of an active compound of formula I can be effected orally or parenterally. An amount of an active compound of formula I is administered such that an effective dose is received, generally a daily dose which, when administered orally to an animal is usually between 0.01 and 20 mg/kg of body weight, preferably between 0.05 and 10 mg/kg of body weight. Conveniently, the medication can be carried in drinking water so that a therapeutic dosage of the agent is ingested with the daily water supply. The agent can be directly metered into drinking water, preferably in the form of a liquid, water-soluble concentrate (such as an aqueous solution of a water soluble salt).

Conveniently, the active compound can also be added directly to the feed, as such, or in the form of an animal feed supplement, also referred to as a premix or concentrate. A premix or concentrate of therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Drinking water and feed effective for treating domestic animals are generally prepared by mixing a compound of the invention with a sufficient amount of animal feed to provide from about $10^{-3}$ to 500 ppm of the compound in the feed or water.

The preferred medicated swine, cattle, sheep and goat feeds generally contain from 1 to 400 grams of active compound per ton of feed, the optimum amount for these animals usually being about 50 to 300 grams per ton of feed.

The preferred poultry and domestic pet feeds usually contain about 1 to 400 grams and preferably 10 to 400 grams of active compound per ton of feed.

For parenteral administration in animals, the compounds of the present invention may be prepared in the form of a paste or a pellet and administered as an implant, usually under the skin of the head or ear of the animal in which increase in lean meat deposition and improvement in lean mean to fat ratio is sought.

In general, parenteral administration involves injection of a sufficient amount of the compounds of the present invention to provide the animal with 0.01 to 20 mg/kg/day of body weight of the active ingredient. The preferred dosage for poultry, swine, cattle, sheep, goats and domestic pets is in the range of from 0.05 to 10 mg/kg/day of body weight of active ingredient.

Preparation of compounds of the invention are illustrated by the following examples and preparations.

PREPARATION 1

2-Methyl-4-chloro-6-phenylpyrrolo [3,2-d] pyrimidine

A mixture of 9 g of Compound (b) and 170 ml of phosphorus oxychloride is heated under boiling for 21 h. After evaporation of the phosphorous oxycloride excess, the reaction mass is diluted with ice water. The precipitate, i.e., the hydrochloride of (c), is mixed with 50 ml water, 100 ml of ethyl acetate are added, and the mixture is neutralized, under thorough stirring and cooling, with ammonia water until and alkaline reaction is obtained (with phenolphthalein). After separation of the layers, the bottom water layer is extracted twice with ethyl acetate (each time 50 ml). The ethyl acetate extracts are combined and evaporated under vacuum. The sediment (c) is filtered off. Yield 7.43 g (76.2%), mp 184–185° C. (from ethyl acetate).

PREPARATION 2

Compounds of the invention may be prepared by the following reaction sequence.

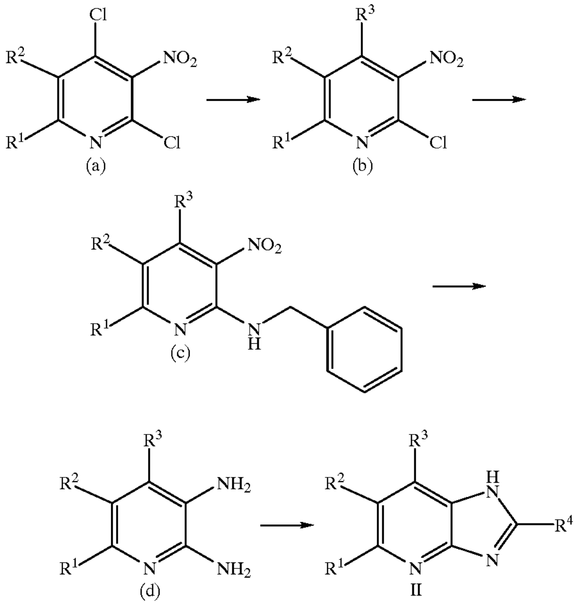
(a) (b) (c) (d) II

Compound (a) may be prepared by the procedure described in *J. Med. Chem.* 37, 1252 (1994) or other standard procedures. The chemist of ordinary skill will recognize that changes in reaction conditions may be necessary when different R-groups are present. For example, protecting groups may be required when one of the R-groups contains an additional functionality. Preparation of Compound II, $R^1$=$CH_3$, $R^2$=H, $R^3$=$N(CH_2)_4$, $R^4$=cyclohexyl is illustrated in Example 5.

Compound (b)

2-Chloro-6-methyl-3-nitro-4-pyrrolidin-1-yl-pyridine

Pyrrolidine (16.7 mL,. 13.1 g) was added to a solution of 20.0 g compound (a) in DMSO (290 mL). The reaction mixture was maintained at room temperature for 2 hours and then added to 400 mL of 1:1 ethyl acetate/hexanes. The resultant solution was washed with three 100-mL portions of saturated aqueous sodium chloride, and the combined organics were back-extracted with 100 mL ethyl acetate. The combined organics were dried over sodium sulfate and were concentrated. The residue was purified by recrystallization from 1:1 ethyl acetate/hexanes. Yield 10.94 g (45%), mp 151–156° C.

Compound (c)

Benzyl-(6-methyl-3-nitro-4-pyrrolidin-1-yl-pyridin-2-yl)-amine

Benzylamine (1.6 mL, 1.5 g) was added to a solution of 0.5 g Compound (a) in 4 mL toluene. The solution was heated to reflux for 42 hours, cooled to room temperature, and poured into 25 mL of water. The mixture was extracted with ethyl acetate (3x25 mL), and the combined extracts were washed with saturated aqueous sodium chloride (50 mL), dried over sodium sulfate, and concentrated. The residue was purified by flash column chromatography (25% ethyl acetate in hexanes). Yield 556 mg (86%)

Compound (d)

6-Methyl-4-pyrrolidin-1-yl-pyridine-2,3-diamine

Palladium on carbon (10%, 250 mg) was added to a solution of Compound (c) (0.77 g) in ethanol (100 mL) in a 250 mL Parr shaker bottle. The flask was charged with hydrogen to a pressure of 45 psi and the reaction mixture was shaken for 14.5 hours at room temperature. The catalyst was removed by filtration through Celite, and the filtrate concentrated in vacuo to provide Compound (d). Yield 630 mg (95%).

PREPARATION 3

Compounds of Formula III may be prepared by the following sequence:

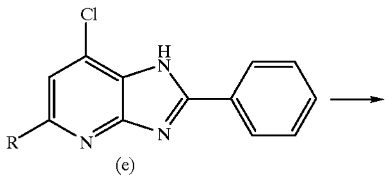

(e)

-continued

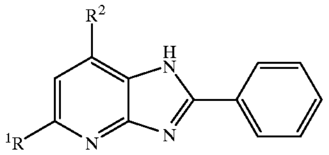

III

Compound (e) may be prepared by the procedure described in *Chem. Pharm. Bull.* 31, 2288 (1983) or other standard procedures. The chemist of ordinary skill will recognize that changes in reaction conditions may be necessary when different R-groups are present. For example, protecting groups may be required when one of the R-groups contains an additional functionality. Preparation of Compound III, $R^1$=$CH_3$, $R^2$=H, $R^3$=$N(CH_2)_4$, $R^4$=phenyl is illustrated by the following examples.

EXAMPLE 1

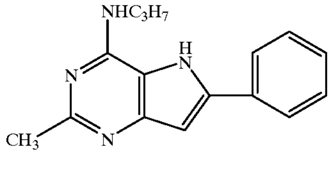

2-Methyl-4-isopropylamino-6-phenylpyrrolo [3,2-d] pyrimidine

A mixture of 1.22 g of the compound of Preparation 1, 0.6 g of isopropylamine, 1 g potash, and 35 ml water was heated in an autoclave at 150 C (bath temperature) for 5 h. The precipitate was filtered off, washed with water and ethyl acetate, and recrystallized from a 75–85% ethanol solution.

EXAMPLE 2

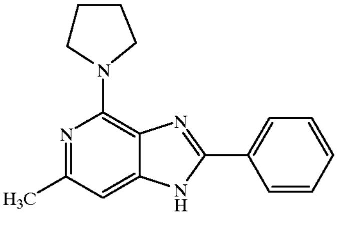

6-Methyl-2-phenyl-4-pyrrolidin-1-yl-1H-imidazo[4, 5-c]pyridine

The title compound was prepared by the procedure of Example 5. Structure was confirmed by MS.

EXAMPLE 3

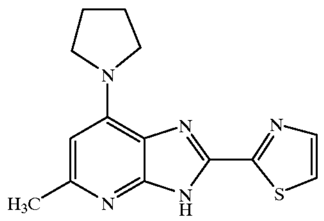

5-Methyl-7-pyrrolidin-1-yl-2-thiazol-2-yl-3H-imidazo[4,5-b]pyridine

The title Compound was prepared by the procedure of Example 5. Structure was confirmed by MS.

EXAMPLE 4

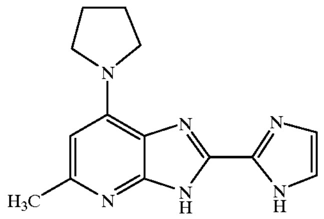

2-(1H-Imidazol-2-yl)-5-methyl-7-pyrrolidin-1-yl-3H-imidazo[4,5-b]pyridine

The title Compound was prepared by the procedure of Example 5. Structure was confirmed by MS.

EXAMPLE 5

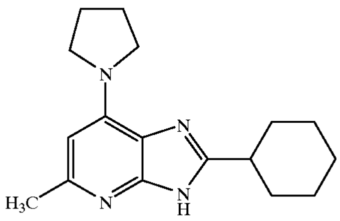

2–Cyclohexyl-5-methyl-7-pyrrolidin-1-yl-3H-imidazo[4,5-b]pyridine

A mixture of 6-methyl-4-pyrrolidin-1-yl-pyridine-2,3-diamine (70 mg), cyclohexanecarboxaldehyde (0.088 mL, 0.082 g) in 1.8 mL nitrobenzene was refluxed for 1 hour. The reaction mixture was cooled to room temperature and loaded directly onto a silica get column. The product was eluted with a dichioromethane grading to 10% methanol/dichloromethane. Fractions containing the product were concentrated in vacuo, taken up in methanol, filtered, and reconcentrated to provide Compound II. Yield 36 mg (35%). MS 285 (M+1)

EXAMPLE 6

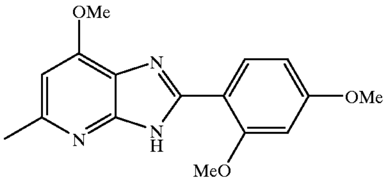

2-(2,4-Dimethoxy-phenyl)-7-methoxy-5-methyl-3H-imidazo[4,5-b]pyridine

The title Compound was prepared by the procedure of Example 5. Structure was confirmed by MS.

EXAMPLE 7

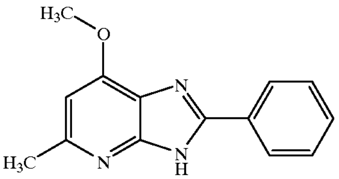

7-Methoxy-5-methyl-2-phenyl-3H-imidazo[4,5-b]pyridine

The title Compound was prepared by the procedure of Example 5. Structure was confirmed by MS.

EXAMPLE 8

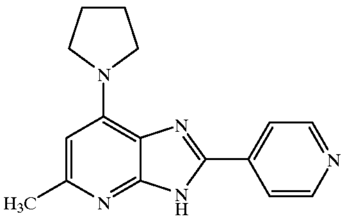

5-Methyl-2-pyridin-4-yl-7-pyrrolidin-1-yl-3H-imidazo[4,5-b]pyridine

The title Compound was prepared by the procedure of Example 5. Structure was confirmed by MS.

EXAMPLE 9

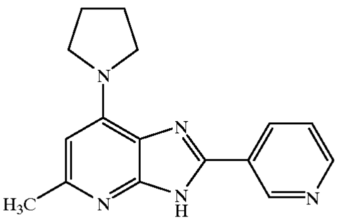

5-Methyl-2-pyridin-3-yl-7-pyrrolidin-1-yl-3H-imidazo[4,5-b]pyridine

The title Compound was prepared by the procedure of Example 5. Structure was confirmed by MS.

EXAMPLE 10

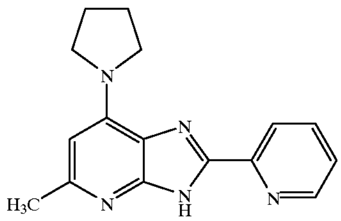

5-Methyl-2-pyridin-2-yl-7-pyrrolidin-1-yl-3H-imidazo[4,5-b]pyridine

The title Compound was prepared by the procedure of Example 5. Structure was confirmed by MS.

EXAMPLE 11

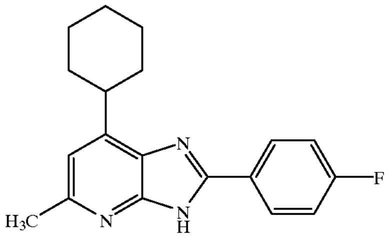

2-(4-Fluoro-phenyl)-5-methyl-7-piperidin-1-yl-3H-imidazo[4,5-b]pyridine

The title Compound was prepared by the procedure of Example 5. Structure was confirmed by MS.

EXAMPLE 12

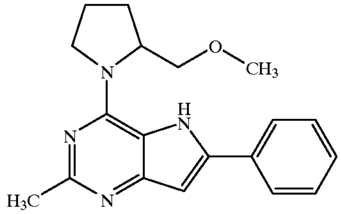

(S)-4-(2-Methoxymethyl-pyrrolidin-1-yl)-2-methyl-6-phenyl-5H-pyrrolo[3,2-d]pyrimidine The title Compound was prepared by the procedure of Example 1. The structure was confirmed by mass spectrometry (MS).

EXAMPLE 13

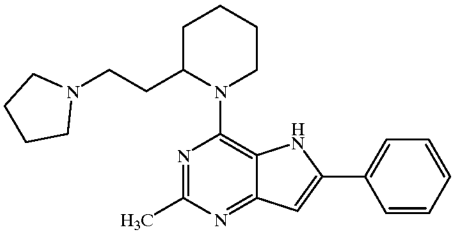

(RS)-2-Methyl-6-Phenyl-4-[2-(2-pyrrolidin-1-yl-ethyl)-piperidin-1-yl]-5H-pyrrolo[3,2-d]pyrimidine The title Compound was prepared by the procedure of Example 1. The structure was confirmed by mass spectrometry (MS).

EXAMPLE 14

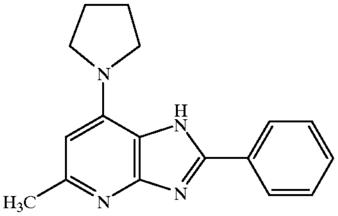

5-Methyl-2-phenyl-7-pyrrolidin-1-yl-1H-imidazo[4,5-b]pyridine

The title Compound was prepared by the procedure of Example 5. Structure was confirmed by MS.

EXAMPLE 15

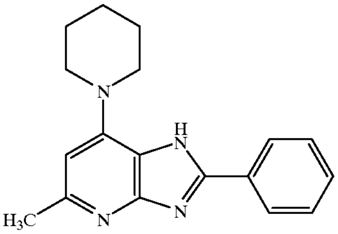

5-Methyl-2-phenyl-7-piperidin-1-yl-1H-imidazo[4,5-b]pyridine

The title Compound was prepared by the procedure of Example 5. Structure was confirmed by MS.

EXAMPLE 16

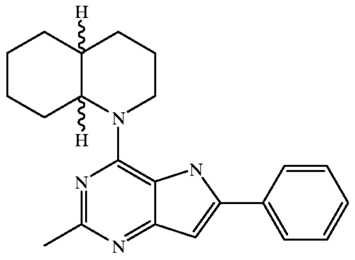

1-(2-Methyl-6-phenyl-5H-pyrrolo[3,2-d]pyrimidin-4-yl)-decahydro-quinoline

The title Compound was prepared by the procedure of Example 1. The structure was confirmed by mass spectrometry (MS).

EXAMPLE 17

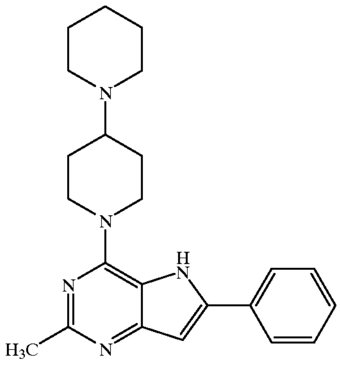

1'-(2-Methyl-6-phenyl-5H-pyrrolo[3,2-d]pyrimidin-4-yl)-[1,4']bipiperidinyl

The title Compound was prepared by the procedure of Example 1. The structure was confirmed by mass spectrometry (MS).

EXAMPLE 18

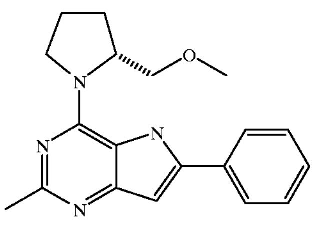

(R)-4-(2-Methoxymethyl-pyrrolidin-1-yl)-2-methyl-6-phenyl-5H-pyrrolo[3,2-d]pyrimidine The title Compound was prepared by the procedure of Example 1. The structure was confirmed by mass spectrometry (MS).

EXAMPLE 19

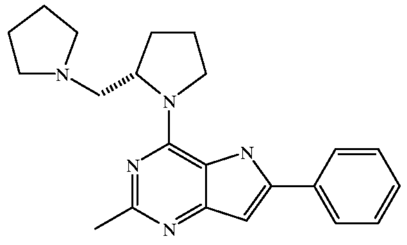

(S)-2-Methyl-6-phenyl-4-(2-pyrrolidin-1-ylmethyl-pyrrolidin-1-yl)-5H-pyrrolo[3,2-d]pyrimidine The title Compound was prepared by the procedure of Example 1. The structure was confirmed by mass spectrometry (MS).

EXAMPLE 20

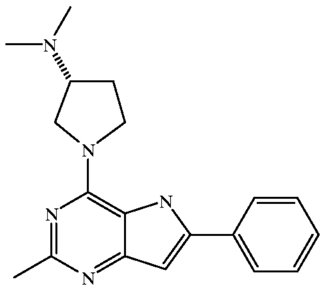

(R)-Dimethyl-[1-(2-methyl-6-phenyl-5H-pyrrolo[3,2-d]pyrimidin-4-yl)-pyrrolidin-3-yl]-amine The title Compound was prepared by the procedure of Example 1. The structure was confirmed by mass spectrometry (MS).

What is claimed is:

1. A compound of the formula:

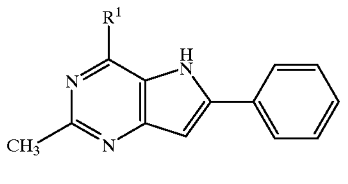

$R^1$ is selected from

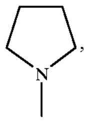,
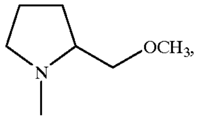

-continued

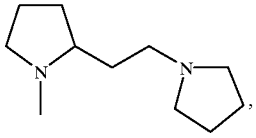,
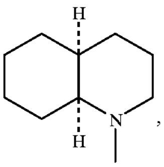,
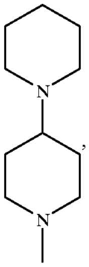,
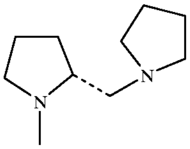, and
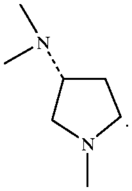.

2. A compound of claim 1 selected from the group consistiug of:

(S)-4-(2-Methoxymethyl-pyrrolidin-1-yl)2-metlyl-6-phenyl-5H-pyrrolo[3,2-d]pyrimidine;

(RS)-2-Methyl-6-phenyl-4-[2-(2-pyrrolidin-1-yl-ethyl)-piperidin-1-yl)-5H-pyrrolo[3,2-d-pyrimidine;

1-(2-Methyl-6-phenyl-5H-pyrrolo[3,2-d]pyrimidin-4-yhl)-decahydro-quinoline;

1'-(2-Methyl-6-phenyl)-5H-pyrrolo[3,2-d]pyrimidin-4-yl)-[1,4']bipiperidinyl;

(R)-4-(2-Methoxymethyl-pyrrolidin-1-yl)-2-methyl-6-phenyl-5H-pyrrolo[3,2-d]pyrimidine;

(S)-2-Methyl-6-phenyl-4-(2-pyrrolidin-1-ylmethyl-pyrrolidin-1-yl)-5H-pyrrolo[3,2-d]pyrimidine; and (R)-Dimethyl-[1-(2-methyl-6-phenyl-5H-pyrrolo[3,2-d]pyrimidin-4-yl)-pyrrolidin-3-yl]-amine.

3. A pharmaceutical composition comprising a compound of claim 1 or a pharmaceutically acceptable salt thereof and a pharmaceutically acceptable carrier.

* * * * *